(12) United States Patent
Doutremepuich (10) Patent No.: US 8,716,341 B2
(45) Date of Patent: May 6, 2014

(54) TOPICALLY APPLICABLE COMPOSITIONS FOR THE TREATMENT OF KERATINIZATION DISORDERS

(75) Inventor: Jean-Daniel Doutremepuich, Peymeinade (FR)

(73) Assignee: Galderma Research & Development, Biot (FR)

( * ) Notice: Subject to any disclaimer, the term of this patent is extended or adjusted under 35 U.S.C. 154(b) by 605 days.

(21) Appl. No.: 12/652,417

(22) Filed: Jan. 5, 2010

(65) Prior Publication Data

US 2010/0144883 A1 Jun. 10, 2010

Related U.S. Application Data

(63) Continuation of application No. PCT/EP2008/058775, filed on Jul. 7, 2008.

(60) Provisional application No. 60/929,652, filed on Jul. 6, 2007.

(51) Int. Cl.
*A61K 31/19* (2006.01)
*A61K 8/72* (2006.01)
*A61P 17/10* (2006.01)

(52) U.S. Cl.
USPC ............................................. 514/569

(58) Field of Classification Search
USPC ........................ 514/569; 424/70.11
See application file for complete search history.

(56) References Cited

U.S. PATENT DOCUMENTS

| 5,212,303 | A * | 5/1993 | Shroot et al. | 544/69 |
| 5,219,877 | A * | 6/1993 | Shah et al. | 514/394 |
| 8,404,202 | B2 * | 3/2013 | Cheng et al. | 423/213.2 |
| 2003/0170196 | A1 * | 9/2003 | Orsoni et al. | 424/70.17 |

FOREIGN PATENT DOCUMENTS

| WO | WO 2006/048747 A1 | 5/2006 |
| WO | WO 2007/031883 A2 | 3/2007 |
| WO | WO 2008/017914 A2 | 2/2008 |

OTHER PUBLICATIONS

Dermatologic disease database (2001) 3 pages.*
Percy SH (2003) 69(4) 277-280.*
International Search Report issued Sep. 21, 2009 by the European Patent Office for PCT/EP2008/058775.
Verschoore et al., "Adapalene 0.1% gel has low skin-irritation potential," *Journal of the American Academy of Dermatology.* Jun. 1997, pp. S104-S109, V. 36, No. 6, Part 2, C.V. Mosby, St. Louis, MO.
Alirezai et al., "Étude Comparative de l'Efficacité et de la Tolérance de Gels D'Adapalène à 0,1 et 0,03 P. 100 et d'un Gel de Trètinoïne à 0,025 P. 100 Dans le Traitement de l'Acné." *Annales de Dermatologie et de Vénéréologie*, Jan. 1, 1996, pp. 165-170, V. 123, No. 3, Elsevier Masson, Paris, France.
Verschoore et al., "Efficacy and safety of CD 271 alcoholic gels in the topical treatment of acne vulgaris," *British Journal of Dermatology*, Apr. 1991, pp. 368-371, V. 124. No. 4.
Ghoshal et al., "Comparative Evaluation of Effectiveness of Adapalene and Azithromycin, Alone or in Combination, in Acne Vulgaris," *Indian Journal of Dermatology*, Oct. 2007, pp. 179-183, V. 52, No. 4, Calcuta National Medical College.
Kawashima et al., "Adapalene Gel 0.1%—Topical Retinoid-Like Molecule-for the Treatment of Japanese Patients with Acne Vulgaris: a Multicenter, Randomized, Investigator-Blinded, Does-Ranging Study," *Skin Research*, Oct. 2007, pp. 494-503, V. 6, No. 5, Japan.

* cited by examiner

*Primary Examiner* — Shirley V Gembeh
(74) *Attorney, Agent, or Firm* — Dentons US LLP (57) ABSTRACT

Topical compositions containing from 0.01% to 0.09% by weight of adapalene or salts thereof are useful for the treatment or prevention of keratinization disorders, particularly acne, and additionally contain at least one gelling agent selected from among carbomers, polysaccharides, cellulose and its derivatives, copolymers of acrylate and of alkyl acrylate, copolymers of acrylamide and of sodium acrylamido-2-methylpropanesulfonate, and xanthan gum.

27 Claims, 3 Drawing Sheets

TOPICALLY APPLICABLE COMPOSITIONS FOR THE TREATMENT OF KERATINIZATION DISORDERS

CROSS-REFERENCE TO EARLIER APPLICATIONS

This application is a continuation of PCT/EP 2008/058775, filed Jul. 7, 2008 and designating the United States (published in the English language on Jan. 15, 2009 as WO 2009/007341 A2), which claims benefit under 35 U.S.C. §119 (e) of U.S. Provisional Application No. 60/929,652, filed Jul. 6, 2007, each hereby expressly incorporated by reference in its entirety and each assigned to the assignee hereof.

BACKGROUND OF THE INVENTION

1. Technical Field of the Invention

The present invention relates to topical compositions for the treatment or prevention of keratinization disorders, to processes for the preparation of such compositions and to their formulation as cosmetic or pharmaceutical products. These compositions are useful, in particular, for the treatment of acne.

2. Description of Background and/or Related and/or Prior Art

Acne is a common multifactor pathology which affects skin rich in sebaceous glands (face, scapular region, arms and intertriginous regions). It is the commonest form of dermatoses. The following five pathogenic factors play a determining role in the formation of acne:
 1. genetic predisposition;
 2. overproduction of sebum (seborrhea);
 3. androgens;
 4. follicular keratinization disorders (comedogenesis); and
 5. bacterial colonization and inflammatory factors.

Several forms of acne exist, all having in common that the pilosebaceous follicles are attacked. In particular, exemplary are acne conglobata, acne keloid on the back of the neck, acne medicamentosa, recurrent acne miliaria, acne necrotica, acne neonatorum, premenstrual acne, occupational acne, acne rosacea, senile acne, solar acne and acne vulgaris.

Acne vulgaris, also known as polymorphous juvenile acne, is the commonest. It comprises four stages:

Stage 1 corresponds to comedonal acne, characterized by a large number of open and/or closed comedones and of microcysts.

Stage 2, or papulopustular acne, is of mild to moderate seriousness. It is characterized by the presence of open and/or closed comedones and of microcysts but also of red papules and of pustules. It mainly affects the face and leaves few scars.

Stage 3, or papulocomedonal acne, is more serious and extends to the back, to the thorax and to the shoulders. It is accompanied by a larger number of scars.

Stage 4, or nodulocystic acne, is accompanied by numerous scars. It exhibits nodules and also large painful purplish pustules.

The various forms of acne described above can be treated with active principles, such as anti-seborrhoeics and anti-infectives, for example benzoyl peroxide (in particular the product Eclaran® marketed by Pierre Fabre), with retinoids, such as tretinoin (in particular the product Retacnyl® marketed by Galderma) or isotretinoin (product Roaccutane® marketed by Laboratoires Roche), or with naphthoic acid derivatives. Naphthoic acid derivatives, such as, in particular, 6-[3-(1-adamantyl)-4-methoxyphenyl]-2-naphthoic acid, commonly known as adapalene (the product Differin® marketed by Galderma), are widely described and recognized as active principles which are as effective as tretinoin in the treatment of acne.

SUMMARY OF THE INVENTION

The present invention features cosmetic or pharmaceutical compositions comprising adapalene or 6-[3-(1-adamantyl)-4-methoxyphenyl]-2-naphthoic acid, the chemical structure of which is as follows:

6-[3-(1-Adamantyl)-4-methoxyphenyl]-2-naphthoic acid (hereinafter adapalene) is a retinoid derived from naphthoic acid having certain characteristics of retinoids. This molecule has been the subject of developments in the topical treatment of acne vulgaris and of retinoid-sensitive dermatoses.

Adapalene was described by the assignee hereof in EP-0199636.

The assignee hereof markets adapalene formulated at a concentration by weight of 0.1% in the form of an alcoholic lotion, of an aqueous gel and of a cream. These compositions are useful for the treatment of acne.

The assignee hereof has also described, in the patent applications of the family of EP-1485080, compositions formulated at a concentration by weight of 0.3% of adapalene with respect to the total weight of the composition. These compositions are useful for the treatment of dermatological conditions with an inflammatory or proliferative component, in particular acne vulgaris.

Several studies have been published comparing the effectiveness and the safety of compositions comprising 0.1% to 0.03% by weight of adapalene and 0.025% by weight of tretinoin in the treatment of acne (Cunliffe W. J. et al., J. Am. Acad. Dermatol., 1997 June, 36(6 Pt. 2): S126-34; Verschoore M. et al., J. Am. Acad. Dermatol. 1997 June; 36 (6 Pt 2): S104-9; Alirezai M. et al. Ann. Dermatol. Venereol., 1996, 123(3), 165-70; Verschoore M. et al., Br. J. Dermatol., 1991, April, 124(4), 368-71). It emerges in particular from these studies that a 0.1% by weight adapalene gel and a 0.025% by weight tretinoin gel are significantly more effective than a 0.03% by weight aqueous adapalene gel against all and the inflammatory lesions of acne vulgaris and that adapalene exhibits a dose-dependant activity in the topical treatment of acne.

One problem which the present invention solves is the provision of compositions which exhibit an effectiveness comparable to that of the compositions of the prior art for the treatment or prevention of keratinization disorders and, preferably, which is less irritating.

It has now been found, surprisingly, that a composition comprising a concentration of adapalene of less than 0.1% to preferably less than 0.07% has an effectiveness comparable to that of a composition comprising 0.1% of adapalene, but with reduced undesirable effects.

Unlike the prior art, novel pharmaceutical compositions have now been developed comprising adapalene at a concentration by weight of 0.001% to 1% to preferably of 0.01% to 0.09% to more preferably still of 0.02 to 0.04% useful for the treatment of keratinization disorders. This is because, surprisingly, it has now been found that the compositions according to the invention exhibit a therapeutic effectiveness comparable to that of the compositions known in the prior art and also good tolerance comparable or superior to those of the known compositions. In particular, the compositions according to the invention are less irritating than a composition comprising 0.1% of adapalene.

These particulars are contrary to the prior art, all the more so as the studies published and indicated above differ from the solution according to the invention, since they show that an aqueous gel comprising 0.03% by weight of adapalene is much less effective, in particular in the treatment of acne, than compositions comprising 0.1% by weight of adapalene.

Thus, the present invention features topical compositions for the treatment or prevention of keratinization disorders, comprising from 0.01% to 0.09% by weight of adapalene or its salts, and which additionally comprise a gelling agent selected from among carbomers, polysaccharides, magnesium aluminum silicates, acrylic polymers coupled to hydrophobic chains, modified starches, polyacrylamides, copolymers of acrylate and of alkyl acrylate, copolymers of acrylamide and of sodium acrylamido-2-methylpropanesulfonate, acrylate/C10-C30 alkyl acrylate crosspolymer or cellulose and its derivatives. In a preferred embodiment, the subject compositions comprise from 0.02% to 0.04% by weight, preferably from 0.025% to 0.035% by weight and preferably approximately 0.03% by weight of adapalene.

DETAILED DESCRIPTION OF BEST MODE
AND SPECIFIC/PREFERRED EMBODIMENTS
OF THE INVENTION

In a particular embodiment of invention, the gelling agent is a carbomer. Preferably, the carbomer ranges from 0.1% to 5% by weight of the composition. In the specific embodiment of gel form the composition comprises from 0.8% to 1.2%, preferably 1%, by weight of carbomer. In the specific embodiment of cream form the composition comprises from 0.45% to 0.5%, preferably 0.45%, by weight of carbomer. In the specific embodiment of lotion form and in that it comprises from 0.1% to 0.5%, preferably 0.1%, by weight of carbomer.

Preferably, the composition is in aqueous form.

In another embodiment, the composition of invention optionally comprises a fatty phase.

In a preferred embodiment the composition comprises additionally a wetting agent selected from among: wetting agents having an HLB (Hydrophilic-Lipophilic Balance) of 7 to 18, or else nonionic wetting agents of the type of polyoxyethylenated and/or polyoxypropylenated copolymers, polyoxyethylene-polyoxypropylene glycol known as Poloxamers and more particularly polyoxyethylene[20]-polyoxypropylene[20] glycol; polyoxyethylene[16]-polyoxypropylene[30] glycol and/or Synperonic PE/L62, glycols, such as propylene glycol or dipropylene glycol, lauroglycol, propylene glycol dipelargonate or ethoxydiglycol.

In a preferred embodiment, the wetting agent is a polyoxyethylene-polyoxypropylene glycol (poloxamer), preferably polyoxyethylene[20]-polyoxypropylene[20] glycol or polyoxyethylene[16]-polyoxypropylene[30] glycol.

According to another embodiment, the compositions of invention comprise additionally a propenetrating agent, a wetting agent, a chelating agent, a preservative and/or a pH adjuster. Preferably, the composition comprises 4% by weight of propylene glycol, as propenetrating agent, 0.2% by weight of poloxamer 182, as wetting agent, 0.1% by weight of disodium edetate, as chelating agent, 0.1% by weight of methyl para-hydroxybenzoate, as preservative, a sufficient amount of sodium hydroxide for the composition to exhibit a pH of 5 and a sufficient amount of water to constitute the composition to 100% of its weight.

In another embodiment, the present invention features the cosmetic or pharmaceutical administration via the topical route of a composition as described above for the treatment or prevention of keratinization disorders. Preferably, the keratinization disorder is acne.

More specifically, the keratinization disorder encompasses acne conglobata, acne keloid on the back of the neck, acne medicamentosa, recurrent acne miliaria, acne necrotica, acne neonatorum, premenstrual acne, occupational acne, acne rosacea, senile acne, solar acne, acne vulgaris, comedonal acne, polymorphous acne, nodulocystic acne or secondary acne, such as solar acne.

In another embodiment, the invention features the cosmetic administration of a composition as described above for the treatment of skin with a tendency towards acne and for combating the greasy appearance of the skin or hair.

In another embodiment, this invention features a process for the preparation of a subject composition which comprises the steps of:

a) adapalene compound is mixed with at least one wetting agent in water, until said retinoid compound is completely dispersed, to obtain the active phase;

b) an aqueous phase comprising water, at least one hydrophilic ingredients is prepared, optionally, add the gelling agent;

c) optionally, for obtaining a solution, the active phase obtained in the step a) is mixed with the aqueous phase obtained in step b);

d) optionally, for obtaining an emulsion, mix, if necessary heat up, at least one emulsifier, at least one lipophilic compound and optionally solid fatty substances until homogenization, to obtain the fatty phase;

e) optionally, for obtaining a gel-cream, mix if necessary heat up, at least one oil and/or solid fatty substance until homogenization, to obtain the fatty phase;

f) in case of gel or gel-cream, mix the active phase obtained in step a) with aqueous phase obtained in step b);

g) optionally, add the gelling agent h) in case of emulsion, said fatty phase obtained in step d) is mixed with the aqueous active phase obtained in step b) to obtain an emulsion;

i) in case of emulsion, the active phase obtained in step a) is mixed with emulsion obtained in step h);

j) in case of gel-cream, the unique ingredient of fatty phase or the fatty phase obtained in step e) is mixed with the phase obtained in step f) or step g);

k) if necessary, heat sensitive additives are added;

l) if necessary, a pH adjuster is introduced into the emulsion obtained in step i) or k) or into the gel obtained in step f) or in the step g) or in the step k) or into the gel-cream obtained in step j) or k) to obtain the desired pH;

m) if necessary, water is added to constitute the remainder.

In another embodiment, the present invention features a non-therapeutic cosmetic treatment method for beautifying the skin or its surface appearance, in which a composition according hereto is applied to the skin and/or its superficial body growths.

In more detail, the present invention provides topical compositions for the treatment or prevention of keratin disorders, comprising from 0.001% to 1% by weight and preferably from 0.01% to 0.09% by weight and more preferably still from 0.02% to 0.04% by weight of adapalene or its salts, and which additionally comprise a gelling agent or a suspending agent selected from:

Carboxyvinyl Polymers either known as carbomers marketed under the generic name of Carbopol®, carbomers described as insensitive to electrolytes, marketed under the trademark Ultrez 20™ or Carbopol ETD2020™ by Noveon, Pemulen TR1 or Pemulen TR2 from Noveon, carbomer 1382, marketed under the trademark Carbopol 1382 by Noveon, carbomer 934P, carbopol 980, carbopol 981 NF, carbopol Ultrez 10, carbopol ETD2020™ or carbopol 974P NF;

polysaccharides, with as non-limiting examples xanthan gum, such as Keltrol T® or Xantural80™ marketed by Kelco, guar gum, chitosans, cellulose and its derivatives, such as hydroxyethylcellulose and in particular hydroxypropylcellulose, such as the product marketed under the trademark Natrosol 250 HHX® by Aqualon or the product marketed under the trademark Methocel E4 Premium™ by Dow Chemical, microcrystalline cellulose and sodium carboxymethyl cellulose, marketed under the trademark Avicel CL-611 by FMC Biopolymer;

the family of carrageenans, in particular divided into four known families: κ, λ, β and ω, such as the Viscarin® products and Gelcarins® products marketed by IMCD;

the family of magnesium aluminum silicates, such as Veegum K™ marketed by Vanderbilt;

the family of acrylic polymers coupled to hydrophobic chains, such as PEG-150/decyl/SMDI copolymer, marketed under the trademark Aculyn 44™ (polycondensate comprising at least as components a polyethylene glycol comprising 150 or 180 mol of ethylene oxide, decyl alcohol and methylenebis(4-cyclohexyl isocyanate) (SMDI), at 35% by weight in a mixture of propylene glycol (39%) and water (26%));

the family of modified starches, such as modified potato starch, marketed under the trademark Structure Solance™, and also their mixtures;

the family of polyacrylamides, such as the sodium acryloyldimethyltaurate copolymer/isohexadecane/polysorbate 80 mixture, marketed under the trademark Simulgen 600™ by Seppic, or the polyacrylamide/C13-14 isoparaffin/laureth-7 mixture, such as, for example, that marketed under the trademark Sepigel 305™ by Seppic;

the family of acrylamide copolymers, such as the copolymer of acrylamide and of sodium acrylamido-2-methylpropanesulfonate in dispersion at 40% in isohexadecane;

the acrylate/C10-C30 alkyl acrylate crosspolymer marketed under the trademark Pemulen TR1 by Noveon.

The preferred gelling agents and/or suspending agents result from the family of polyacrylamides, such as Simulgel 600PHA™ or Sepigel 305™; carbomers described as insensitive to electrolytes, such as Carbopol 1382™, carbomers marketed in particular under the trademarks Carbopol 974P NF and Carbopol 980; polysaccharides, such as xanthan gum; cellulose derivatives, such as hydroxypropylmethylcellulose or hydroxyethylcellulose; and magnesium aluminum silicates, alone or as a mixture; the combination of carbomer/acrylate/C10-C30 alkyl acrylate crosspolymer with xanthan gum and hydroxyethylcellulose or also the combination of carbomer 1382 with xanthan gum and carbomer 981 NF.

The gelling agent as described above can be used at preferred concentrations ranging from 0.001 to 15%.

The present invention will be more fully described in the description which follows and the figures which accompany it, in which:

The term "comparable effectiveness" means an effectiveness equal to or of the same order of magnitude as that of the compositions of the prior art. For example, when the effectiveness is evaluated as percentage of reduction in lesions, two values are comparable when they differ by 0 to 7 points and, preferably, by less than 2 points. The compositions according to the invention can offer, advantageously, for a reduced amount of active principle, an effectiveness comparable to that of the compositions of the prior art, and also a superior or comparable tolerance.

The term "adapalene salts" means the salts formed with a pharmaceutically acceptable base, in particular inorganic bases, such as sodium hydroxide, potassium hydroxide and ammonia, or organic bases, such as lysine, arginine or N-methylglucamine. The term "adapalene salts" also means the salts formed with fatty amines, such as dioctylamine and stearylamine.

Advantageously, the compositions according to the invention do not comprise any depigmenting agent distinct from the adapalene.

According to a specific embodiment of the invention, the adapalene is in dispersed form in the composition.

Throughout the present text, unless otherwise specified, it is understood that, when concentration ranges are given, they include the upper and lower limits of said range. Similarly, unless otherwise indicated, the proportions of the various constituents of the composition are expressed as percentage by weight (m/m) of the total weight of said composition.

The compositions according to the invention comprise from 0.001% to 1% by weight of adapalene and preferably from 0.01% to 0.09% by weight and more preferably still from 0.02% to 0.04% by weight of adapalene or its salts and preferably from 0.025% to 0.035% by weight and more preferably still approximately 0.03% by weight.

The compositions according to the invention preferably comprise from 0.001% to 15% by weight and preferably from 0.1% to 5% by weight of gelling agent or of a suspending agent.

The compositions according to the invention are useful for topical application and for the treatment of the skin and mucous membranes. Same can be provided in the form of ointments, creams, milks, salves, powders, impregnated pads, solutions, gels, cream gels, sprays, foams, lotions or suspensions. They can also be provided in the form of suspensions of microspheres or nanospheres or of lipid or polymer vesicles or of polymer patches and of hydrogels which make controlled release possible. It can also be provided in the anhydrous form, in the aqueous form, in the alcoholic form or in the form of an emulsion. In a preferred embodiment of the invention, the pharmaceutical compositions are provided in the form of a gel, of a cream, of a solution or of a lotion. Preferably, the compositions according to the invention is in the aqueous form.

According to a preferred embodiment, the compositions according to the invention are in the gel form and comprise from 0.8% to 1.2%, preferably 1%, by weight of gelling agent, preferably a carbomer.

According to a preferred embodiment, the compositions according to the invention are in the cream form and comprise from 0.45% to 0.5%, preferably 0.5%, by weight of a suspending agent, preferably a carbomer.

According to a preferred embodiment, the compositions according to the invention are in the lotion form and comprise from 0.1% to 0.5%, preferably 0.1%, by weight of a suspending agent, preferably a carbomer.

The pharmaceutical compositions according to the invention can optionally comprise a fatty phase to obtain emulsion forms, such as creams, milks or "light" emulsions.

The formulation of adapalene as a "light" emulsion is advantageous for topical treatments, such as that of acne, as, while contributing emollience, it prevents in particular an excessively greasy feel from being left to remain on the skin.

The term "light emulsion" means an emulsion comprising a low proportion of fatty phase, the aqueous phase remaining predominant.

The term "emulsion" means a liquid system comprising two fluids which are insoluble or only slightly soluble in one another and in which one of the fluids is dispersed in the other as microscopic particles. Preferably, the emulsions comprise at least one emulsifier, a polar hydrophilic, preferably aqueous phase and a non-polar fatty phase. Preferably, they are provided in the form of "oil-in-water" (O/W) or "water-in-oil" (W/O) emulsions.

A cream is a formulation which comprises water and oil and is stabilized with an emulsifier. Lipophilic creams are "water-in-oil" (W/O) emulsions and hydrophilic creams are referred to as "oil-in-water" (O/W) emulsions. W/O creams generally have absorbent bases (petrolatum, ceresin, lanolin, and the like). O/W creams have, as base, mono-, di- and triglycerides of fatty acids or of fatty alcohols with soap, alkyl sulfates or ethers of alkyl polycyclols used as emulsifiers. The creams can recreate a disturbed hydrolipidic film or rehydrate the horny layer by virtue of their occlusive power. They can also act as protective cleaning agents or as vehicles for transporting therapeutic substances.

One embodiment, in particular, is an emulsion comprising:
    adapalene;
    at least one hydrophilic phase;
    at least one fatty phase;
    at least one emulsifier.

More particularly, the hydrophilic phase of the compositions according to the invention as defined above is an aqueous phase.

The compositions according to the invention can in particular comprise, in relation to adapalene and at least one emulsifier, one or more of the following ingredients:
    a) one or more gelling agents and/or suspending agents and/or pH-independent gelling agents,
    b) one or more chelating agents,
    c) one or more wetting agents,
    d) one or more lipophilic excipients of which the fatty phase is composed,
    e) an aqueous phase,
    f) one or more additives.

The compositions according to the invention are preferably in the form of an oil-in-water (O/W) emulsion.

The compositions according to the invention can comprise at least one emulsifier.

Preferably, the emulsifier is distinct from the wetting agents.

The term "emulsifiers" means amphiphilic compounds having a hydrophobic part, which has an affinity for the oil, and a hydrophilic part, which has an affinity for the water, thus creating a link from the two phases. Thus, ionic or nonionic emulsifiers stabilize emulsions (O/W) by being adsorbed at the interface and by forming lamellar layers of liquid crystals.

The emulsifying power of nonionic emulsifiers is closely related to the polarity of the molecule. This polarity is defined by the HLB (Hydrophilic-Lipophilic Balance).

A high HLB indicates that the hydrophilic fraction is predominant and, conversely, a low HLB indicates that the lipophilic part is predominant. For example, HLB values greater than approximately 10 correspond to hydrophilic surfactants.

Emulsifiers can be categorized, according to their structure, under the generic terms "ionic" (anionic, cationic or amphoteric) or "nonionic". Nonionic emulsifiers are emulsifiers which do not dissociate into ions in water and are thus insensitive to variations in pH.

Nonionic emulsifiers are particularly well suited to the preparation of emulsions of oil-in-water type. Thus, the emulsifying system comprises at least one nonionic emulsifier with a hydrophilic predominant fraction, that is to say exhibiting a high HLB of greater than approximately 10.

Exemplary are, as non-limiting examples of nonionic emulsifiers exhibiting a high HLB, sorbitan esters, such as PEO(20) sorbitan monooleate, marketed under the trademark Tween 80™ (HLB=15), or PEO(20) sorbitan monostearate, marketed under the trademark Tween 60™ (HLB=14.9), fatty alcohol ethers, such as PEO(21) stearyl ether (HLB=15.5), marketed under the trademark Brij 721 by Uniqema, or ceteareth-20, marketed under the trademark Eumulgin B2PH™ by Cognis (HLB of 15.5), polyoxyethylene glycol esters, such as glyceryl stearate and PEG 100 stearate, marketed under the trademark Arlacel 165 FL® (HLB=11) by Uniqema, or PEG 6 stearate and PEG 32 stearate, marketed under the trademark Tefose 1500® (HLB=10) by Gateffossé, or sugar esters with a high HLB, such as PEG 20 methyl glucose sesquistearate, marketed under the trademark glucamate SSE20 (HLB=15) by Amerchol, and sucrose laurate, marketed under the trademark Surfhope C-1216® (HLB=16), and sucrose stearate, marketed under the trademark Surfhope C-1811® (HLB=11), by Gattefossé.

Preferably, the said nonionic emulsifiers with a high HLB exhibit an HLB of from 10 and 18.

Examples of nonionic emulsifiers with a low HLB (lipophilic emulsifiers), are sorbitan esters, such as sorbitan monostearate (HLB=4.7), marketed under the trademark Span 60™ by Uniqema, glycerol esters, such as glycerol monostearate, marketed under the trademark Cutina GMS-VPH™ (HLB=3.8) by Cognis, polyethylene glycol esters, such as PEG-6 isostearate, marketed under the trademark Olépal isostéarique (HLB=8) by Gattefossé, or sugar esters with a low HLB, such as methyl glucose sesquistearate, marketed under the trademark Glucate SS (HLB=6) by Amerchol and sucrose dilaurate, marketed under the name of Surfhope C-1205 (HLB=5), and sucrose tristearate, marketed under the trademark Surfhope C-1803 (HLB=3), by Gattefossé. Preferably, the said nonionic emulsifiers exhibiting a low HLB exhibit an HLB of less than 10.

The nonionic emulsifiers can be used alone or as a mixture of two or more of them to form the emulsifying system.

Preferred emulsifying systems, comprise one or more "nonionic emulsifier with a high HLB"/"nonionic emulsifier with a low HLB" pairs; the system can in particular be a nonionic emulsifying system comprising at least one nonionic emulsifier exhibiting an HLB of greater than approximately 10 and at least one nonionic emulsifier exhibiting an HLB of less than approximately 10.

The ratio of each of the two emulsifiers forming the above-mentioned pair is generally determined by the calculation of the HLB required for the fatty phase used.

Exemplary are, as preferred emulsifiers, hydrophilic emulsifiers of the following types: glyceryl stearate & PEG-100 stearate, marketed under the trademark Arlacel 165FL™ by Uniqema, or PEG 6 stearate and PEG 32 stearate, marketed under the trademark Tefose 1500™ by Gattefossé; or lipophilic emulsifiers of the following types: sucrose esters, such as Glucate SS™ (methyl glucose sesquistearate) and Glucamate SSE 20™ (PEG 20 methyl glucose sesquistearate) marketed by Amerchol, polyoxyethylene (21) stearyl ether, marketed under the trademark Brij721™ by Uniqema, or ceteareth-20, marketed under the trademark Eumulgin B2PH™ by Cognis.

According to the invention, the preferred concentrations of emulsifiers are from 0.001% to 20% by weight. More preferably, the concentration is from 1% to 15% by weight and preferably from 3% to 11% by weight, with respect to the total weight of the composition.

The pharmaceutical compositions according to the invention can additionally comprise inert additives or combinations of these additives, such as:

wetting agents, such as polyoxyethylene polyoxypropylene glycol, for example Poloxamer 182 or poloxamer 124, or propylene glycol;

propenetrating agents;

preservatives, such as esters of parahydroxybenzoic acid, for example methyl parahydroxybenzoate;

stabilizing agents;

pH-regulating agents, such as sodium hydroxide;

chelating agents, such as disodium edetate;

UV-A and UV-B screening agents;

and antioxidants, such as α-tocopherol, butylated hydroxyanisole or butylated hydroxytoluene, superoxide dismutase or ubiquinol.

Exemplary are, among chelating agents, ethylenediaminetetraacetic acid (EDTA), diethylenetriaminepentaacetic acid (DTPA), ethylenediamined(o-hydroxyphenylacetic acid) (EDDHA), (2-hydroxyethyl)ethylenediaminetriacetic acid (HEDTA), ethylenediamined(o-hydroxy-p-methylphenylacetic acid) (EDDHMA) and ethylenediamined(5-carboxy-2-hydroxyphenylacetic acid) (EDDCHA).

Exemplary are, as preferred chelating agent, ethylenediaminetetraacetic acid (EDTA), marketed in particular under the trademark Titriplex III®.

Preferred wetting agents, the role of which is to reduce the surface tension and to make possible greater spreading of the liquid, are compounds such as propylene glycol, dipropylene glycol, propylene glycol dipelargonate, lauroglycol and ethoxydiglycol, alone or as a mixture.

The wetting power is the tendency of a liquid to spread over a surface.

Preferably, the wetting agents are wetting agents having an HLB (Hydrophilic-Lipophilic Balance) of 7 to 18, or else nonionic wetting agents of the type of polyoxyethylenated and/or polyoxypropylenated copolymers (mention will be made, as non-limiting examples, of polyoxyethylene-polyoxypropylene glycol known as Poloxamers and more particularly polyoxyethylene[20]-polyoxypropylene[20] glycol (poloxamer 124 known also as Synperonic P/L44; polyoxyethylene[16]-polyoxypropylene[30] glycol (poloxamer 182) and/or Synperonic PE/L62, marketed by Uniqema), glycols, such as propylene glycol or dipropylene glycol, lauroglycol, propylene glycol dipelargonate or ethoxydiglycol. They must be liquid, so as to be easily incorporated in the composition without it being necessary to heat it.

Preferred wetting agents, the role of which is to reduce the surface tension and to make possible greater spreading of the liquid, are compounds of the family of the Poloxamers and/or glycols and more particularly Synperonic PE/L44 and/or Synperonic PE/L62 and/or compounds such as propylene glycol, dipropylene glycol, propylene glycol dipelargonate, lauroglycol or ethoxydiglycol.

Exemplary are, as preferred wetting agent, propylene glycol and Synperonic PE/L44 (Poloxamer 124™).

The concentration of wetting agents in the compositions according to the invention is from 0.001% to 20% by weight, preferably from 0.1% to 10% by weight and more preferably from 2% to 7% by weight, with respect to the total weight of the composition.

Exemplary are, among preservatives, benzoic acid and its derivatives with benzyl alcohol, benzalkonium chloride, sodium benzoate, bronopol, chlorhexidine, chlorocresol and its derivatives, ethyl alcohol, phenethyl alcohol, phenoxyethanol, potassium sorbate, diazolidinylurea or parabens, such as propylparaben or methylparaben, taken alone or as mixtures.

Exemplary are, as preferred preservative, parabens and phenoxyethanol or benzalkonium chloride, alone or as a mixture.

The compositions according to the invention can also comprise a fatty phase. This fatty phase can comprise, for example, vegetable, mineral, animal or synthetic oils, silicone oils and mixtures thereof.

Exemplary are, as examples of mineral oil, liquid paraffins with different viscosities, such as Primol 352®, Marcol 82® or Marcol 152®, marketed by Esso.

Exemplary are, as vegetable oil, sweet almond oil, palm oil, soybean oil, sesame oil or sunflower oil.

Exemplary are, as animal oil, lanoline, squalene, fish oil or mink oil, with, as derivative, the squalene marketed under the trademark Cosbiol® by Laserson.

Exemplary are, as synthetic oil, an ester, such as cetearyl isononanoate, for example the product marketed under the trademark Cetiol SNPH® by Cognis France, diisopropyl adipate, for example the product marketed under the trademark Ceraphyl 230® by ISF, isopropyl palmitate, for example the product marketed under the trademark Crodamol IPP® by Croda, or caprylic/capric triglyceride, such as Miglyol 812®, marketed by Hüls/Lambert Rivère.

Exemplary are, as silicone oil, a dimethicone, such as the product marketed under the trademark Dow Corning 200 Fluid®, or a cyclomethicone, such as the product marketed under the trademark Dow Corning 244 Fluid® by Dow Corning or the product marketed under the trademark ST-Cyclométhicone 5NF® by Dow Corning.

Solid fatty substances may also be included, such as natural or synthetic waxes. In this case, one skilled in the art will adjust the heating temperature of the preparation as a function of the presence or absence of the solids.

For the compositions according to the invention, liquid paraffins and more particularly Marcol 152® and Miglyol 812® are preferred.

The hydrophilic phase of the emulsion according to the invention is preferably aqueous and may therefore comprise water. This water may in particular be a floral water such as cornflower water, or a natural mineral water or spring water, for example selected from Vittel water, water from the Vichy basin, Uriage water, La Roche Posay water, Avène water or Aix-les-Bains water.

Said aqueous phase may be present at a content of from 10% to 90% by weight, relative to the total weight of the composition, preferably from 20% to 80% by weight.

The compositions of the invention can, in addition, in particular comprise any additive conventionally used in the cosmetic or pharmaceutical field, such as neutralizing agents of standard inorganic or organic base or acid type (as examples, triethanolamine, 10% sodium hydroxide solution, succinic acid/sodium succinate buffer, citric acid/sodium citrate buffer), humectants and/or emollients (as example glycerol), sunscreens, antioxidants, fillers, electrolytes, colorants, standard inorganic or organic bases or acids, fragrances, essential oils, cosmetic active principles, moisturizing agents, vitamins, essential fatty acids, sphingolipids, self-tanning compounds, such as DHA, soothing and skin-protecting agents, and optionally a stabilizing agent for benzoyl peroxide (as example, sodium docusate or sodium C14-16 olefinsulfonate).

Of course, one skilled in the art will take care to select this or these optional additional compounds and/or their amounts such that the advantageous properties of the compositions according to the invention are not, or not substantially, detrimentally affected.

The concentrations of the said additives of the composition are from 0.001% to 20% by weight, with respect to the total weight of the composition.

The compositions according to the invention can comprise a second active principle in addition to adapalene and in particular an antibacterial compound, such as an antibiotic, or benzoyl peroxide (BPO).

According to a specific embodiment of the invention, the composition comprises adapalene and BPO. The adapalene is in an amount as defined above and the amount of BPO is from 0.0001% to 20% by weight of benzoyl peroxide, with respect to the total weight of the composition. Preferably, the amount of BPO is from 0.001% to 10% by weight, with respect to the total weight of the composition, and more preferably from 2% to 10% by weight and more particularly from 2.5% to 5% by weight, with respect to the total weight of the composition.

The benzoyl peroxide can just as easily be employed in the free form or else in an encapsulated form, for example in a form adsorbed on or absorbed in any pore support. It can, for example, be benzoyl peroxide encapsulated in a polymeric system composed of porous microspheres, such as, for example, microsponges marketed under the trademark Microsponges P009A Benzoyl Peroxide by Cardinal Health.

Advantageously, the particle size of the retinoid and of the benzoyl peroxide is such that at least 80% by number of the particles and preferably at least 90% by number of the particles have a diameter of less than 25 µm and at least 99% by number of the particles have a diameter of less than 100 µm.

Of course, one skilled in the art will take care to select the optional compound or compounds to be added to these compositions such that the advantageous properties intrinsically attached to the present invention are not, or not substantially, detrimentally affected by the envisaged addition.

In particular, the compositions according to the invention can be in the form of an aqueous gel and can comprise in particular one or more gelling agents selected from carbomer 940 (Noveon Carbopol 980) and propylene glycol. The compositions according to the invention can be in the form of a cream and can comprise in particular one or more gelling agents selected from carbopol 940 (Noveon Carbopol 980) and one or more ingredients selected from perhydrosqualene, cyclomethicone, PEG-20 methylglucose sesquistearate and methylglucose sesquistearate. The compositions according to the invention can also be in the form of an aqueous lotion and comprise in particular one or more gelling agents selected from carbomer 940 (Noveon Carbopol 980) and propylene glycol.

Preferably, in addition to approximately 0.03% by weight of adapalene and a gelling agent, the compositions according to the invention comprise a propenetrating agent, a wetting agent, a chelating agent, a preservative and/or a pH adjuster. According to a preferred embodiment, the composition comprises 4% by weight of propylene glycol, as propenetrating agent, 0.2% by weight of poloxamer 182, as wetting agent, 0.1% by weight of disodium edetate, as chelating agent, 0.1% by weight of methyl para-hydroxybenzoate known as methylparaben, as preservative, a sufficient amount of sodium hydroxide for the composition to exhibit a pH of 5 and a sufficient amount of water to complete the composition to 100% of its weight.

The present invention also features the composition as described above, formulated as medicaments.

This invention also features a process for the preparation of a composition as described above. A composition according to the invention is prepared in 1 or several stages according to the formulation form selected, the 2 additional stages being carried out solely for the preparation of the forms of emulsion type, such as creams, lotions or cream gels.

Preferably, in the compositions of the invention, the adapalene is in a dispersed form.

The other excipients and additives of an optional nature will be introduced as a function of the chemical nature of the compounds and of the formulation form selected.

For more clarity in the following descriptions of processes, by lipophilic compound, is meant a substance having an affinity for, tending to combine with, or capable of dissolving in lipids, fat or oils.

By hydrophilic ingredients, is meant a substance having a strong affinity for water, tending to dissolve in, mix with, or be wetted by water.

The preparation of a composition according to the invention is carried out according to a general process as follows:

a) adapalene compound is mixed with at least one wetting agent in water, until said retinoid compound is completely dispersed, to obtain the active phase;

b) an aqueous phase comprising water, at least one hydrophilic ingredients is prepared, optionally, add the gelling agent;

c) optionally, for obtaining a solution, the active phase obtained in the step a) is mixed with the aqueous phase obtained in step b);

d) optionally, for obtaining an emulsion, mix, if necessary heat up, at least one emulsifier, at least one lipophilic compound and optionally solid fatty substances until homogenization, to obtain the fatty phase;

e) optionally, for obtaining a gel-cream, mix if necessary heat up, at least one oil and/or solid fatty substance until homogenization, to obtain the fatty phase;

f) in case of gel or gel-cream, mix the active phase obtained in step a) with aqueous phase obtained in step b);

g) optionally, add the gelling agent h) in case of emulsion, said fatty phase obtained in step d) is mixed with the aqueous active phase obtained in step b) to obtain an emulsion;

i) in case of emulsion, the active phase obtained in step a) is mixed with emulsion obtained in step h);

j) in case of gel-cream, the unique ingredient of fatty phase or the fatty phase obtained in step e) is mixed with the phase obtained in step f) or step g);

k) if necessary, heat sensitive additives are added;

l) if necessary, a pH adjuster is introduced into the emulsion obtained in step i) or k) or into the gel obtained in step f) or in the step g) or in the step k) or into the gel-cream obtained in step j) or k) to obtain the desired pH;

m) if necessary, water is added to make up the remainder.

The present invention also features the cosmetic or pharmaceutical administration, whether regime or regimen, via the topical route, of a composition as defined above for the treatment or prevention of keratinization disorders.

This invention also features the formulation of adapalene at a final concentration by weight of from 0.02% to 0.04%, preferably from 0.025% to 0.035% to more preferably of approximately 0.03% into medicaments useful for the treatment or prevention of keratinization disorders.

According to the present invention, the keratinization disorders are selected from:

acne conglobata, acne keloid on the back of the neck, acne medicamentosa, recurrent acne miliaria, acne necrotica, acne neonatorum, premenstrual acne, occupational acne, acne rosacea, senile acne, solar acne, acne vulgaris, comedonal acne, polymorphous acne, nodulocystic acne or secondary acne, such as solar acne;

Darier's disease;

palmoplantar keratodermas and keratosis pilaris;

leukoplakias and leukoplakia-like states, and lichen planus;

pigmentary disorders, such as melasma;

disorders related to aging, such as blemishes or wrinkles;

promoting healing and preparing the skin for operations;

all benign or malignant, severe and extensive, dermatological proliferations.

The compositions according to the invention are particularly suitable for the treatment and prevention of acne, such as acne vulgaris, in particular for the treatment of light to moderate acne vulgaris.

To further illustrate the present invention and the advantages thereof, the following specific examples are given, of various formulations of compositions comprising 0.03% of adapalene and also results showing the therapeutic or cosmetic effectiveness of the subject compositions and the good tolerance by the patients treated, it being understood that same are intended only as illustrative and in nowise limitative. In said examples to follow, all parts and percentages are given by weight, unless otherwise indicated.

EXAMPLES

The examples illustrate various specific topical formulations comprising from 0.02% to 0.04% of adapalene.

Example 1

Composition in the Cream Form

| | |
|---|---|
| Adapalene | 0.3 mg |
| Carbomer 934P | 4.5 mg |
| Disodium edetate | 1 mg |
| PEG 20 methylglucose sesquistearate | 35 mg |
| Methyl glucose sesquistearate | 35 mg |
| Glycerol | 30 mg |
| Methylparaben | 2 mg |
| Cyclomethicone | 130 mg |
| Perhydrosqualene | 60 mg |
| Phenoxyethanol | 5 mg |
| Propylparaben | 1 mg |
| Sodium hydroxide 10% w/w | q.s. for pH 6.5 +/− 0.3 |
| Purified water | q.s. for 1 g |

Example 2

Composition in the Solution Form

| | |
|---|---|
| Adapalene | 0.3 mg |
| Carbomer 940 | 1 mg |
| PEG 400 | 700 mg |
| Ethanol | q.s. for 1 g |
| Purified water | q.s. for 1 g |

Example 3

Composition in a Lotion Form

| Constituents | Content (% w/w) |
|---|---|
| Adapalene | 0.03 |
| Methylparaben | 0.15 |
| Disodium edetate | 0.10 |
| Methocel E4M Premium | 0.10 |
| Pemulen TR1 | 0.30 |
| Olépal Isostéarique | 2.00 |
| Cosbiol | 8.00 |
| Cetiol SN PH | 8.00 |
| Propylparaben | 0.05 |
| Sodium hydroxide, 10% w/w | q.s. for pH 5.5 ± 0.5 |
| Purified water | q.s. for 100 |

Example 4

Composition in the Lotion Form

| Constituents | Content (% w/w) |
|---|---|
| Adapalene | 0.03 |
| Methylparaben | 0.15 |
| Simulgel 600 PHA | 1.00 |
| Brij 721 | 3.00 |
| Arlacel 165FL | 3.00 |
| Disodium edetate | 0.10 |
| Propylparaben | 0.05 |
| Cosbiol | 5.00 |
| Cetiol SN PH | 5.00 |
| Sodium hydroxide 10% w/w | q.s. for pH 5.5 ± 0.5 |
| Purified water | q.s. for 100 |

Example 5

Composition in the Lotion Form

| Constituents | Content (% w/w) |
| --- | --- |
| Adapalene | 0.04 |
| Methylparaben | 0.15 |
| Simulgel 600 PHA | 1.00 |
| Brij 721 | 3.00 |
| Arlacel 165FL | 3.00 |
| Disodium edetate | 0.10 |
| Propylparaben | 0.05 |
| Cosbiol | 5.00 |
| Cetiol SN PH | 5.00 |
| Sodium hydroxide, 10% w/w | q.s. for pH 5.5 ± 0.5 |
| Purified water | q.s. for 100 |

Example 6

Composition in the Aqueous Gel Form

| Constituents | Content (% w/w) |
| --- | --- |
| Adapalene | 0.3 mg |
| Carbomer 940 | 11 mg |
| Disodium edetate | 1 mg |
| Methylparaben | 1 mg |
| Polyoxyethylene(20)/ polyoxypropylene(20) glycol (Poloxamer124) | 2 mg |
| Propylene glycol | 40 mg |
| Sodium hydroxide, 10% w/w | q.s. for pH 5.0 ± 0.3 |
| Purified water | q.s. for 1 g |

Example 7

Effectiveness of a Gel Comprising 0.03% of Adapalene and Comparison with the Gel Comprising 0.1% of Adapalene Study:

A study was carried out on 238 patients divided at random into three groups, including two of 80 patients and one of 78 patients, respectively subjected to a 0.1% by weight adapalene gel, to a 0.03% by weight adapalene gel and to the adapalene-free vehicle gel. The composition of the 0.03% gel applied in the context of this study is shown in Example 1c. The composition of the 0.1% gel and the composition of the vehicle-alone gel are the same, with the exception of the amount of adapalene, which is respectively 1 mg and 0 mg.

This investigator-blinded and vehicle-controlled randomized multicenter study with parallel-group comparison was designed to evaluate and compare the effectiveness and the safety of the 0.1% to 0.03% adapalene gels in patients affected by light to moderate acne vulgaris versus the vehicle-alone gel.

The treatment was applied topically once daily for 12 weeks.

B) Results on the Total Number of Lesions:

The total number of lesions decreased significantly in the population studied at the end of the treatment with the 0.03% by weight adapalene gel according to the invention and with the 0.1% adapalene gel, in comparison with the treatment with the vehicle-alone gel. The total number of lesions was counted for the patients of each group during the study. From these values, the percentage of reduction in the total number of lesions was calculated (Cochran-Mantel-Haenszel test) during the study, with respect to the total number of lesions before treatment, in the population of patients studied.

Figure 1:
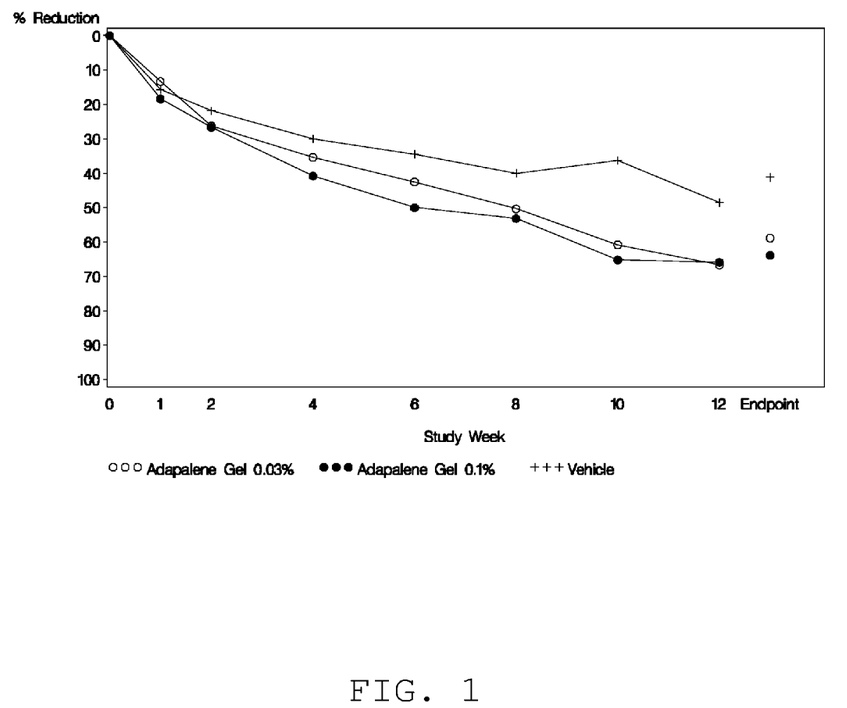
FIG. 1 is a graph on which have been plotted the curves representing the median of the percentage of reduction in the total number of lesions in each group of patients studied and its change during the study.

FIG. 1 shows a graph on which have been plotted the curves representing the median of the percentage of reduction in the total number of lesions in each group of patients and its change during the study. On this graph, the percentage of reduction is shown on the ordinate and the time is shown in weeks on the abscissa. The curve of solid circles is this percentage over time in the group of patients treated with a 0.1% by weight adapalene gel, the curve of open circles is this percentage over time in the group of patients treated with a 0.03% by weight adapalene gel and the curve of crosses is this percentage over time in the group of patients treated with a vehicle-alone gel.

This graph shows that the effectiveness of the 0.03% by weight adapalene gel according to the invention, in terms of median percentage of reduction in the total lesions related to acne vulgaris, is comparable to that of the 0.1% adapalene gel, in particular after 12 weeks of treatment, with more than 65% reduction in the total number of lesions with the two treatments. Specifically, this median percentage of reduction is 59 after 12 weeks of treatment with a 0.03% adapalene gel, 64% with a 0.1% adapalene gel and 41% with the vehicle-alone gel. From this graph, the effectiveness of the 0.03% adapalene gel is also comparable to that of the 0.1% adapalene gel at 8 weeks of treatment, with respectively 50.4% to 53.2% (median value) reduction, against 40% with the vehicle-alone gel.

The results of the study also show that the same proportion of patients in the group treated with the 0.1% adapalene gel and in the group treated with the 0.03% by weight adapalene gel according to the invention exhibits an "excellent" degree of improvement, that is to say a percentage of reduction in the total number of lesions of greater than 75%. Specifically, this proportion is 32.5% of the patients in each of these groups, against 15.4% of the patients of the group treated with the vehicle-alone gel. This underlines that the effectiveness of the 0.03% by weight adapalene gel according to the invention is comparable with that of a 0.1% adapalene gel, in particular for obtaining a percentage of reduction in the total number of lesions of greater than 75%.

C) Results on the Number of Non-Inflammatory Lesions:

The number of non-inflammatory lesions significantly decreased in the population studied at the end of the treatment with the 0.03% by weight adapalene gel according to the invention and with the 0.1% adapalene gel, by comparison with the treatment with the vehicle-alone gel. The number of non-inflammatory lesions was counted for the patients of each group during the study. From these values, the percentage of reduction in the number of non-inflammatory lesions was calculated during the study, with respect to the number of non-inflammatory lesions before treatment, in the population of patients studied.

Figure 2:
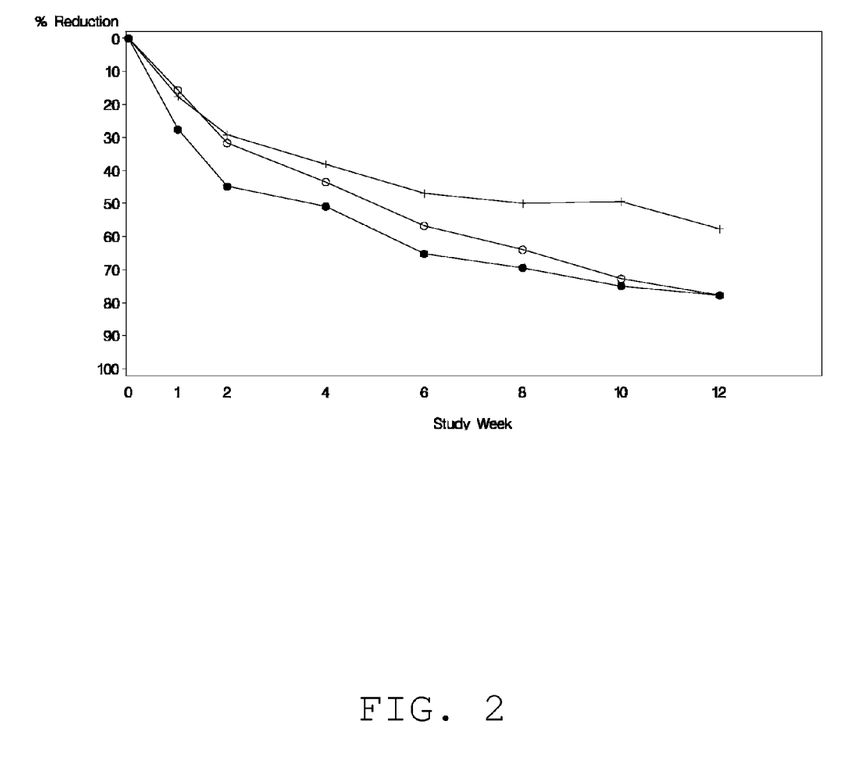
FIG. 2 is a graph on which have been plotted the curves representing the median of the percentage of reduction in the number of non-inflammatory lesions in each group of patients studied and its change during the study.

FIG. 2 shows a graph on which have been plotted the curves representing the median percentage of reduction in the number of non-inflammatory lesions in each group of patients and its change during the study. On this graph, the percentage of reduction is shown on the ordinate and the time is shown in weeks on the abscissa. The curve of solid circles is this percentage over time in the group of patients treated with a 0.1% by weight adapalene gel, the curve of open circles is this percentage over time in the group of patients treated with a 0.03% by weight adapalene gel and the curve of crosses is this percentage over time in the group of patients treated with a vehicle-alone gel.

This graph shows that the effectiveness of the 0.03% by weight adapalene gel according to the invention, in terms of median percentage of reduction in the non-inflammatory lesions related to acne vulgaris, is comparable with that of the 0.1% adapalene gel, in particular after 12 weeks of treatment, with more than 76% reduction (median value) in the total number of lesions with the two treatments. Specifically, this median percentage of reduction is 75% after 12 weeks of treatment with the 0.03% adapalene gel according to the invention, and also with the 0.1% adapalene gel, and 50% with the vehicle-alone gel.

D) Results on the Number of Inflammatory Lesions:

The number of inflammatory lesions decreased in the population studied at the end of the treatment with the 0.03% by weight adapalene gel according to the invention and with the 0.1% adapalene gel, by comparison with the treatment with the vehicle-alone gel. The number of inflammatory lesions was counted and the percentage of reduction in the number of inflammatory lesions was calculated as described in Sections B and C.

Figure 3:
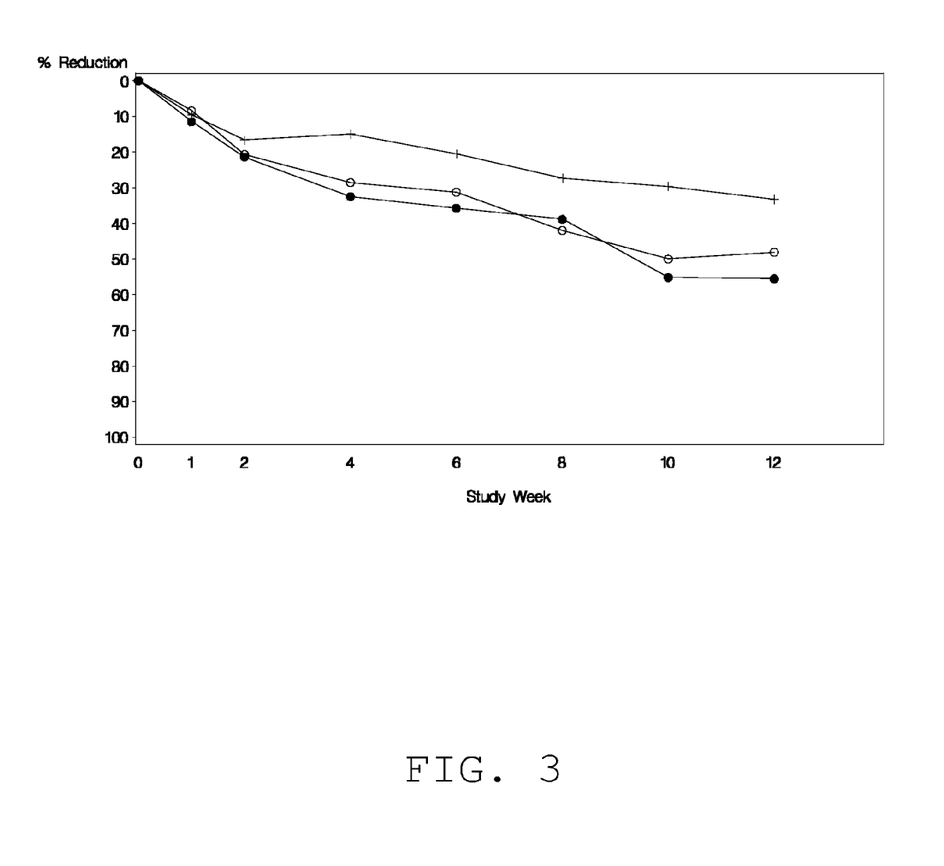
FIG. 3 is a graph on which have been plotted the curves representing the median of the percentage of reduction in the number of inflammatory lesions in each group of patients studied and its change during the study.

FIG. 3 shows a graph on which have been plotted the curves representing the median percentage of reduction in the number of inflammatory lesions in each group of patients and its change in the course of the study. This graph is presented like those of FIGS. 1 and 2.

This graph shows that the effectiveness of the 0.03% by weight adapalene gel, in terms of median percentage of reduction in the inflammatory lesions related to acne vulgaris, is comparable with that of the 0.1% adapalene gel, in particular at 8 weeks of treatment. Specifically, after 8 weeks of treatment, this percentage is 42% with the 0.03% adapalene gel according to the invention, 38.9% with the 0.1% adapalene gel and 27.3% with the vehicle-alone gel. After 12 weeks of treatment, this percentage is 48% with the 0.03% adapalene gel, 54% with the 0.1% adapalene gel and 30% with the vehicle-alone gel. Thus, the 0.03% by weight adapalene gel has an effectiveness comparable to that of the 0.1% gel for reducing the number of inflammatory lesions related to acne vulgaris after 8 weeks of treatment and an effectiveness comparable to that of the 0.1% gel after 12 weeks of treatment.

The two adapalene concentrations were well tolerated.

The scores of severity of erythema, desquamation, dryness and burning feeling during the treatment are presented in FIG. 4. Generally, local tolerance is good for all the treatments, with moderate scores of tolerance at each visit and the lowest score for erythema, desquamation, dryness and burning feeling light and transitory and without irritation. Burning feeling and pruritus had a low incidence which was similar in the two 0.1% to 0.03% groups. The incidence of erythema was similar in the three groups.

Each patent, patent application, publication, text and literature article/report cited or indicated herein is hereby expressly incorporated by reference in its entirety.

While the invention has been described in terms of various specific and preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for treating acne afflicting a subject, said method comprising topically applying once daily for a period of 12 weeks onto said subject's skin, an effective amount of a pharmaceutical composition,
    which comprises an amount of from 0.02% to 0.04% by weight of adapalene or pharmaceutically acceptable salt thereof,
    and which additionally comprises at least one gelling agent selected from the group consisting of carbomers, polysaccharides, magnesium aluminum silicates, acrylic polymers coupled to hydrophobic chains, modified starches, polyacrylamides, copolymers of acrylamide and of sodium acrylamido-2-methylpropanesulfonate, acrylate/C10-C30 alkyl acrylate crosspolymers and cellulose gelling agents, formulated into a topically applicable, pharmaceutically acceptable carrier therefor,
    wherein said adapalene or salt thereof is the only active anti-acne agent in the composition and applied in the method,
    wherein said adapalene or salt thereof is the only agent for lessening irritation in the composition and applied in the method,
    wherein said amount of adapalene or salt thereof is sufficient to provide therapeutic effectiveness to said method of applying said composition comparable to that of a method of topically applying once daily a composition comprising 0.1% by weight of adapalene or salt thereof while being comparable or superior in terms of lessening irritation, and
    wherein comparable therapeutic effectiveness is shown by a reduction in total lesion counts, in inflammatory lesion counts, or in non-inflammatory lesion counts, in a group of such subjects achieved by said method of applying said composition after 12 weeks of treatment comparable to the reduction in total lesion counts, in inflammatory lesion counts or in non-inflammatory lesion counts, respectively, achieved by a method of topically applying once daily a composition comprising 0.1% by weight of adapalene after 12 weeks of treatment.

2. The method as defined by claim 1, wherein said pharmaceutical composition comprises an amount of 0.03% by weight of adapalene.

3. The method as defined by claim 1, wherein said at least one gelling agent comprises a carbomer.

4. The method as defined by claim 3, wherein said carbomer comprises from 0.1% to 5% by weight of said pharmaceutical composition.

5. The method as defined by claim 1, wherein said pharmaceutical composition is formulated in gel form and comprises from 0.8% to 1.2% by weight of carbomer.

6. The method as defined by claim 1, wherein said pharmaceutical composition is formulated in cream form and comprises from 0.45% to 0.5% by weight of carbomer.

7. The method as defined by claim 1, wherein said pharmaceutical composition is formulated in lotion form and comprises form 0.1% to 0.5% by weight of carbomer.

8. The method as defined by claim 1, wherein said pharmaceutical composition is formulated in aqueous form.

9. The method as defined by claim 1, wherein said pharmaceutical composition further comprises a fatty phase.

10. The method as defined by claim 1, wherein said pharmaceutical composition further comprises at least one wetting agent selected from the group consisting of wetting agents having an Hydrophilic-Lipophilic Balance of 10-18 which are nonionic wetting agents selected from the group consisting of polyoxyethylenated and polypropylenated copolymers, and glycols.

11. The method as defined by claim 10, said at least one wetting agent comprising a polyoxyethylene-polyoxypropylene glycol (poloxamer).

12. The method as defined by claim 11, comprising polyoxyethylene[20]-polyoxypropylene[20] glycol.

13. The method as defined by claim 10, wherein the pharmaceutical composition comprises a glycol.

14. The method as defined by claim 13, wherein the glycol comprises propylene glycol, dipropylene glycol, lauroglycol, propylene glycol dipelargonate or ethoxydiglycol.

15. The method as defined by claim 1, wherein said pharmaceutical composition further comprises a propenetrating agent, a wetting agent, a chelating agent, a preservative and/or pH adjuster.

16. The method as defined by claim 15, wherein the pharmaceutical composition comprises 4% by weight of propylene glycol, as propenetrating agent, 0.2% by weight of poloxamer 182, as wetting agent, 0.1% by weight of disodium edetate, as chelating agent, 0.1% by weight of methyl para-hydroxybenzoate, as preservative, a sufficient amount of sodium hydroxide for the composition to exhibit a pH of 5 and a sufficient amount of water to constitute the composition to 100% of its weight.

17. A method for treating acne afflicting a subject, said method comprising topically applying once daily for a period of 12 weeks onto said subject's skin an effective amount of a pharmaceutical composition,
which comprises an amount of from 0.02% to 0.04% by weight of adapalene or pharmaceutically acceptable salt thereof,
and which additionally comprises at least one gelling agent selected from the group consisting of carbomers, formulated into a topically applicable, pharmaceutically acceptable carrier therefor;
wherein said adapalene or salt thereof is the only active anti-acne agent in the composition and applied in the method;
wherein said adapalene or salt thereof is the only agent for lessening irritation in the composition and applied in the method;
wherein said amount of adapalene or salt thereof is sufficient to provide therapeutic effectiveness to said method of applying said composition comparable to that of a method of topically applying once daily a composition comprising 0.1% by weight of adapalene or salt thereof while being comparable or superior in terms of lessened irritation; and
wherein comparable therapeutic effectiveness is shown by a reduction in total lesion counts, in inflammatory lesion counts or in non-inflammatory lesion counts, in a group of such subjects achieved by said method of applying said composition after 12 weeks of treatment comparable to the reduction in total lesion counts, in inflammatory lesion counts or in non-inflammatory lesion counts, respectively, achieved by a method of topically applying once daily a composition comprising 0.1% by weight of adapalene after 12 weeks of treatment.

18. The method as defined by claim 17, wherein said pharmaceutical composition comprises an amount of 0.03% by weight of adapalene.

19. The method as defined by claim 18, wherein said pharmaceutical composition comprises from 0.1% to 5% by weight of at least one carbomer.

20. The method as defined by claim 19, wherein said pharmaceutical composition is formulated in gel form and comprises from 0.8% to 1.2% by weight of at least one carbomer.

21. The method as defined by claim 18, wherein said pharmaceutical composition further comprises at least one wetting agent selected from the group consisting of wetting agents having a Hydrophilic-Lipophilic Balance of 10 to 18 which are nonionic wetting agents selected from the group consisting of polyoxyethylenated and polyoxypropylenated copolymers, and glycols.

22. The method as defined by claim 21, wherein said at least one wetting agent comprises a polyoxyethylene-polyoxypropylene glycol (poloxamer).

23. The method as defined by claim 18, wherein said pharmaceutical composition further comprises a propenetrating agent, a wetting agent, a chelating agent, a preservative, and optionally a pH adjuster.

24. The method as defined by claim 23, wherein said pharmaceutical composition comprises propylene glycol, as propenetrating agent; polyoxyethylene[20]-polyoxypropylene[20] glycol, as wetting agent; disodium edetate, as chelating agent; methyl para-hydroxybenzoate, as preservative; a sufficient amount of sodium hydroxide for the composition to exhibit a pH of 5; and a sufficient amount of water to constitute the composition to 100% of its weight.

25. The method as defined by claim 24, wherein said pharmaceutical composition comprises 4% by weight of propylene glycol, as propenetrating agent; 0.2% by weight of polyoxyethylene[20]-polyoxypropylene[20] glycol, as wetting agent; 0.1% by weight of disodium edetate, as chelating agent; 0.1% by weight of methyl para-hydroxybenzoate, as preservative; a sufficient amount of sodium hydroxide for the composition to exhibit a pH of 5; and a sufficient amount of water to constitute the composition to 100% of its weight.

26. A method for treating acne afflicting a subject, said method comprising topically applying once daily for a period of 8 weeks onto said subject's skin an effective amount of a pharmaceutical composition,
which comprises an amount of from 0.02% to 0.04% by weight of adapalene or pharmaceutically acceptable salt thereof,
and which additionally comprises at least one gelling agent selected from the group consisting of carbomers, formulated into a topically applicable, pharmaceutically acceptable carrier therefor;
wherein said adapalene or salt thereof is the only active anti-acne agent in the composition and applied in the method;
wherein said adapalene or salt thereof is the only agent for lessening irritation in the composition and applied in the method;
wherein said amount of adapalene or salt thereof is sufficient to provide therapeutic effectiveness to said method of applying said composition comparable to that of a method of topically applying once daily a composition comprising 0.1% by weight of adapalene or salt thereof while being comparable or superior in terms of lessened irritation; and
wherein comparable therapeutic effectiveness is shown by a reduction in total lesion counts or in inflammatory lesion counts, in a group of such subjects achieved by said method of applying said composition after 8 weeks of treatment comparable to the reduction in total lesion counts or in inflammatory lesion counts, respectively, achieved by a method of topically applying once daily a composition comprising 0.1% by weight of adapalene after 8 weeks of treatment.

27. The method as defined by claim 26, wherein said pharmaceutical composition comprises an amount of 0.03% by weight of adapalene.

* * * * *